United States Patent
Tokimitsu

(10) Patent No.: US 10,866,219 B2
(45) Date of Patent: Dec. 15, 2020

(54) METHOD FOR DETECTING TRIFLURIDINE- AND/OR TIPIRACIL-RELATED SUBSTANCE

(71) Applicant: TAIHO PHARMACEUTICAL CO., LTD., Chiyoda-ku (JP)

(72) Inventor: Yoshinori Tokimitsu, Tokushima (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 15/952,367

(22) Filed: Apr. 13, 2018

(65) Prior Publication Data
US 2019/0195840 A1 Jun. 27, 2019

(30) Foreign Application Priority Data
Dec. 22, 2017 (JP) ................... 2017-246043

(51) Int. Cl.
*G01N 30/89* (2006.01)
*B01J 20/281* (2006.01)
(Continued)

(52) U.S. Cl.
CPC ........... *G01N 30/48* (2013.01); *A61K 31/513* (2013.01); *A61K 31/7072* (2013.01); *B01J 20/283* (2013.01); *B01J 20/287* (2013.01); *B01J 20/28083* (2013.01); *C07H 19/06* (2013.01); *G01N 30/89* (2013.01);
(Continued)

(58) Field of Classification Search
None
See application file for complete search history.

(56) References Cited

U.S. PATENT DOCUMENTS

| 5,744,475 A | 4/1998 | Yano et al. |
| 6,159,969 A | 12/2000 | Yano et al. |

(Continued)

FOREIGN PATENT DOCUMENTS

| CN | 103788075 A | 5/2014 |
| CN | 105198947 A | 12/2015 |

(Continued)

OTHER PUBLICATIONS

Sahu, S.K. et al. Development and validation of a RP-HPLC-PDA method for simultaneous determination of trifluridine and tipiracil in pure and pharmaceutical dosageform, International Journal of Novel Trends in Pharmaceutical Sciences, vol. 7(5), pp. 145-151 (Year: 2017).*

(Continued)

*Primary Examiner* — Xiaoyun R Xu
(74) *Attorney, Agent, or Firm* — Oblon, McClelland, Maier & Neustadt, L.L.P.

(57) ABSTRACT

This invention provides a method that is capable of detecting a trifluridine-related substance and a tipiracil-related substance contained in a sample containing trifluridine or a salt thereof and tipiracil or a salt thereof using the same procedure. The method is for detecting a trifluridine-related substance or a tipiracil-related substance or both, the method comprising the step of subjecting a sample containing trifluridine or a salt thereof and tipiracil or a salt thereof to high-performance liquid chromatography using a mobile phase composed of an organic phase and an aqueous phase.

21 Claims, 2 Drawing Sheets

(51) Int. Cl.

| | |
|---|---|
| *C07H 19/06* | (2006.01) |
| *B01J 20/287* | (2006.01) |
| *B01J 20/283* | (2006.01) |
| *A61K 31/7072* | (2006.01) |
| *B01J 20/28* | (2006.01) |
| *A61K 31/513* | (2006.01) |
| *G01N 30/00* | (2006.01) |
| *G01N 30/02* | (2006.01) |
| *G01N 30/34* | (2006.01) |

(52) U.S. Cl.
CPC ........... *B01J 2220/54* (2013.01); *G01N 30/34* (2013.01); *G01N 2030/027* (2013.01); *G01N 2030/486* (2013.01)

(56) References Cited

U.S. PATENT DOCUMENTS

| | | |
|---|---|---|
| 6,294,535 B1 | 9/2001 | Yano et al. |
| 2007/0212763 A1 | 9/2007 | Kai et al. |
| 2014/0356431 A1 | 12/2014 | Ohnishi |
| 2014/0363512 A1 | 12/2014 | Ohnishi et al. |
| 2019/0212309 A1 | 7/2019 | Takeda et al. |
| 2019/0369063 A1 | 12/2019 | Takeda et al. |

FOREIGN PATENT DOCUMENTS

| | | | |
|---|---|---|---|
| CN | 105461772 A | 4/2016 | |
| CN | 106749194 A * | 5/2017 | ........... C07D 403/06 |
| CN | 106749194 A | 5/2017 | |
| CN | 103788075 B | 3/2018 | |
| CN | 108203437 A | 6/2018 | |
| EP | 1 849 470 A1 | 10/2007 | |
| JP | 60-56996 | 4/1985 | |
| JP | 61-010565 A | 1/1986 | |
| JP | 4437786 B2 | 3/2010 | |
| JP | 4441313 B2 | 3/2010 | |
| JP | 4603274 B2 | 12/2010 | |
| WO | WO 96/30346 A1 | 10/1996 | |
| WO | WO 2006/080327 A1 | 8/2006 | |
| WO | WO 2013/122134 A1 | 8/2013 | |
| WO | WO 2013/122135 A1 | 8/2013 | |
| WO | 2019/124544 A1 | 6/2019 | |
| WO | 2019/135405 A1 | 7/2019 | |

OTHER PUBLICATIONS

Voorde, J.V. et al. Mycoplasma hyorhinis-encoded cytidine deaminase efficiently inactivates cytosine-based anticancer drugs, FEBS OPen Bio, vol. 5, pp. 634-639 (Year: 2015).*
Tauraite, D., et al. Synthesis of novel derivatives of 5-carboxyuracil, Chemija, vol. 26(2), pp. 120-125. (Year: 2015).*
Horsch et al., "Influence of radiation sterilization on the stability of trifluorothymidine", International Journal of Pharmaceutics, 2001, vol. 222, pp. 205-215.
Moiseev et al., "Structure of Chemical Compounds, Methods of Analysis and Process Control", Pharmaceutical Chemistry Journal, 2007, vol. 41, No. 1, pp. 25-33.
Tanaka et al., "Repeated oral dosing of TAS-102 confers high trifluridine incorporation into DNA and sustained antitumor activity in mouse models", Oncology Reports, 2014, vol. 32, pp. 2319-2326.
Sakamoto et al., "Crucial roles of thymidine kinase 1 and deoxyUTPase in incorporating the antineoplastic nucleosides trifluridine and 2'-deoxy-5-fluorouridine into DNA", International Journal of Oncology, 2015, vol. 46, pp. 2327-2334.
Fresco-Taboada et al., "Development of an immobilized biocatalyst based on Bacillus psychrosaccharolyticus NDT for the preparative synthesis of trifluridine and decytabine", Catalysis Today, 2015, vol. 259, pp. 197-204.
Rizwan et al., "Analytical Method Development and Validation for the Simultaneous Determination of Tipiracil and Trifluridine in Bulk and Capsule Dosage Form by RP-HPLC Method", International Journal of Innovative Pharmaceutical Sciences and Research, 2017, vol. 5, No. 9, pp. 32-42.
Goday et al., "Development and Validation of Stability Indicating RP-HPLC Method for the Simultaneous Estimation of Combination Drugs Trifluridine and Tipiracil in Bulk and Pharmaceutical Dosage Forms", International Journal of Research in Applied, Natural and Social Sciences, 2017, vol. 5, Issue 2, pp. 93-103.
Jogi et al., "An Effective and Sensitive Stability Indicating Chromatographic Approach Based on RP-HPLC for Trifluridine and Tipiracil in Bulk and Pharmaceutical Dosage Form", International Journal of Research in Pharmacy and Chemistry, 2017, vol. 7, No. 1, pp. 63-70.
Paw et al., "Determination of trifluridine in eye drops by high-performance liquid chromatography", Pharmazie, 1997, vol. 52, No. 7, pp. 551-552.
Briggle et al., "Analysis of 5-Fluoro-2'-Deoxycytidine and 5-Trifluoromethyl-2'-Deoxycytidine and Their Related Antimetabolites by High-Performance Liquid Chromatography", Journal of Chromatography, 1986, vol. 381, pp. 343-355.
Riegel et al., "Determination of trifluorothymidine in the eye using high-performance liquid chromatography", Journal of Chromatography, 1991, vol. 568, pp. 467-474.
Balansard et al., "Determination of ophthalmic therapeutic trifluorothymidine and its degradation product by reversed-phase high-performance liquid chromatography", Journal of Chromatography, 1985, vol. 348, pp. 299-303.
Kawauchi et al., "Determination of a new thymidine phosphorylase inhibitor, TPI, in dog and rat plasma by reversed-phase ion-pair high-performance liquid chromatography", Journal of Chromatography B, 2001, vol. 751, pp. 325-330.
Lee et al., "Human mass balance study of TAS-102 using $^{14}$C analyzed by accelerator mass spectrometry", Cancer Chemother Pharmacol, 2016, vol. 77, pp. 515-526.
Coulier et al., "Simultaneous Quantitative Analysis of Metabolites Using Ion-Pair Liquid Chromatography-Electrospray Ionization Mass Spectrometry", Analytical Chemistry, vol. 78, No. 18, 2006, pp. 6573-6582.
Nikitas et al., "Multillinear gradient elution optimization in reversed-phase liquid chromatography based on logarithmic retention models: Application to separation of a set of purines, pyrimidines and nucleosides", Journal of Chromatography A, 1218, 2011, pp. 5658-5663.
Office Action dated Oct. 1, 2018, in co-pending U.S. Appl. No. 16/040,734.
Lee, M.G., "A High Pressure Liquid Chromatographic Method for the Determination of Trifluorothymidine Degradation in Aqueous Solution", International Journal of Pharmaceutics, 1980, vol. 5, pp. 19-24.
Haginoya, N. et al., "Nucleosides and Nucleotides. 160. Synthesis of Oligodeoxyribonucleotides Containing 5-(N-Aminoalkyl) carbamoyl-2'-deoxyuridines by a New Postsynthetic Modification Method and Their Thermal Stability and Nuclease-Resistance Properties", Bioconjugate Chemistry, 1997, vol. 8, No. 3, pp. 271-280.
International Search Report dated Mar. 26, 2019 in PCT/JP2018/047223 filed Dec. 21, 2018.
Jones, M F., "The stability of trifluorothymidine: hydrolysis in buffered aqueous solutions", Journal of Pharmacy and Pharmacology, 1981, vol. 33, No. 5, pp. 274-278.
International Search Report dated Apr. 9, 2019 in PCT/JP2019/000010 filed Jan. 4, 2019.
Rammler, et al., "Studies on Polynucleotides. XVI. Specific Synthesis of the $C_{3'}$—$C_{5'}$ Interribonucleotidic Linkage. Examination of Routes Involving Protected Ribonucleosides and Ribonucleoside-3' Phosphates. Syntheses of Uridylyl-(3'→5')-adenosine, Uridylyl-(3'→5')-adenosine and Related Compunds", J. AM. CHEM. SOC., vol. 84, 1962, pp. 3112-3122.
Office Action dated Oct. 1, 2019 in co-pending U.S. Appl. No. 16/442,993.
Fukushima et al., "Structure and Activity of Specific Inhibitors of Thymidine Phosphorylase to Potentiate the Function of Antitumor 2'-Deoxyribonucleosides", Biochemical Pharmacology, vol. 59, pp. 1227-1236, 2000.

(56) References Cited

OTHER PUBLICATIONS

Hoff et al., "Phase I safety and pharmacokinetic study of oral TAS-102 once daily for fourteen days in patients with solid tumors", Proceedings of the 11th NCI AACR Symposium, pp. 13, 2000.
Dwivedy et al., "Safety and Pharmacokinetics (PK) of an Antitumor/Antiangiogenic Agent, TAS-102: A Phase I Study for Patients (PTS) with Solid Tumors", Proceedings of ASCO, vol. 20, pp. 18, 2001.
Thomas et al., "A dose-finding, safety and pharmacokinetics study of TAS-102, an antitumor/antiangiogenic agent given orally on a once-daily schedule for five days every three weeks in patients with solid tumors", Proceedings of the American Association for Cancer Research, vol. 43, pp. 21, 2002.
Shirasaka et al., "Preclinical and Clinical Practice of S-1 in Japan", Fluoropyrimidines in Cancer Therapy, pp. 285-302, 2004.
Emura et al., "An optimal dosing schedule for a novel combination antimetabolite, TAS-102, based on its intracellular metabolism and its incorporation into DNA", International Journal of Molecular Medicine, pp. 249-255, 2004.

* cited by examiner

METHOD FOR DETECTING TRIFLURIDINE- AND/OR TIPIRACIL-RELATED SUBSTANCE

TECHNICAL FIELD

The present invention relates to a method for measuring trifluridine- and tipiracil-related substances contained in a pharmaceutical preparation containing trifluridine and tipiracil.

BACKGROUND ART

Related substances in medicinal drugs are generally measured by liquid chromatography, and a normal- or reversed-phase column system is commonly used with a mobile phase composed of a liquid mixture of water and an organic solvent.

Lonsurf (registered trademark), a product of the Applicant, is a pharmaceutical preparation comprising trifluridine and tipiracil.

The medicinal drug comprising trifluridine and tipiracil is sold as an antitumor agent, and there have been reports on this pharmaceutical preparation (Patent Literature (PTL) 1, PTL 2, PTL 3, and PTL 4). Known trifluridine-related substances are 5-trifluoromethyluracil (trifluorothymine) and 5-carboxyuracil, and Non-Patent Literature (NPL) 1 reports the use of high-performance liquid chromatography to measure these related substances. As a tipiracil-related substance, 5-chloro-6-{(2-oxopyrrolidin-1-yl)methyl}pyrimidine-2,4-(1H,3H)-dione is known as a synthetic intermediate of tipiracil (PTL 5).

To measure 5-trifluoromethyluracil, which is a trifluridine-related substance, NPL 2 reports various conditions for high-performance liquid chromatography using acetonitrile.

To measure the amount of trifluridine incorporated into tumor cells, NPL 3 reports conditions for high-performance liquid chromatography using acetonitrile.

To determine the substrate specificity of TK1 of trifluridine, NPL 4 reports conditions for high-performance liquid chromatography using acetonitrile.

To confirm trifluridine in enzyme synthesis, NPL 5 reports conditions for high-performance liquid chromatography with the use of trimethyl ammonium acetate in a gradient mode.

For quantitative measurement of trifluridine and tipiracil contained in Lonsurf, NPL 6, NPL 7, and NPL 8 report conditions for high-performance liquid chromatography using acetonitrile.

Regarding trifluridine as eye drops, NPL 9 and NPL 10 report conditions for high-performance liquid chromatography using methanol.

Regarding trifluridine, NPL 11, NPL 12, PTL 6, and PTL 13 report conditions for high-performance liquid chromatography using a mobile phase to which an acetate buffer, trifluoroacetic acid, or acetic acid is added.

Further, PTL 7 discloses performing high-performance liquid chromatography to confirm the purity of trifluridine; however, PTL 7 nowhere discloses conditions for the chromatography.

For measuring tipiracil in plasma, NPL 13 reports conditions for high-performance liquid chromatography using methanol to which ammonium acetate is added, and NPL 14 reports conditions using acetonitrile. Further, 5-chloro-6-(chloromethyl)pyrimidine-2,4(1H,3H)-dione is known as a synthetic intermediate of tipiracil (PTL 4).

For production control of the medicinal drug above, it is necessary to separate the peaks of the principal components and the peaks of the principal component-related substances from each other, and perform analysis within a short period of time with sufficient reproducibility. However, there has been no report on a method for detecting trifluridine- and tipiracil-related substances by high-performance liquid chromatography under the same conditions for each substance. Further, it has been unknown that 2'-deoxy-5-methoxycarbonyluridine can be contained in a medicinal drug comprising trifluridine and tipiracil.

CITATION LIST

Patent Literature

PTL 1: WO2013/122134
PTL 2: WO2013/122135
PTL 3: WO2006/080327
PTL 4: WO96/30346
PTL 5: CN106749194A
PTL 6: CN105198947A
PTL 7: CN105461772A
PTL 8: Japanese Patent No. 4603274
PTL 9: Japanese Patent No. 4441313
PTL 10: Japanese Patent No. 4437786

Non-Patent Literature

NPL 1: P. Horsch et al., International Journal of Pharmaceutics 222 (2001), pp. 205-215
NPL 2: D. V. Moiseev et al., Pharmaceutical Chemistry Journal 41, 1 (2007), pp. 25-33
NPL 3: N. TANAKA et al., Oncology Reports 32 (2014), pp. 2319-2326
NPL 4: K. SAKAMOTO et al., International Journal of Oncology 46 (2015), pp. 2327-2334
NPL 5: A. Fresco-Taboada et al., Catalysis Today 259 (2015), pp. 197-204
NPL 6: M. S. H. Rizwan et al., International Journal of Innovative Pharmaceutical Sciences and Research 5 (2017), pp. 32-42
NPL 7: S. GODAY et al., International Journal of Research in Applied, Natural and Social Sciences 5 (2017), pp. 93-104
NPL 8: K. Jogi et al., International Journal of Research in Pharmacy and Chemistry 7 (2017), pp. 63-70
NPL 9: B. Paw et al., Pharmazie 7 (1997), pp. 551-552
NPL 10: T. Briggle et al., Journal of Chromatography 381 (1986), pp. 343-355
NPL 11: M. Riegel et al., Journal of Chromatography 568 (1991), pp. 467-474
NPL 12: G. Balansard et al., Journal of Chromatography 348 (1985), pp. 299-303
NPL 13: T. Kawauchi et al., Journal of Chromatography 751 (2001), pp. 325-330
NPL 14: J. Lee et al., Cancer Chemother Pharmacol 77 (2016), pp. 515-526

SUMMARY OF INVENTION

Technical Problem

The problem to be solved by the present invention is to provide a method that is capable of detecting a trifluridine-related substance and a tipiracil-related substance contained in a sample containing trifluridine or a salt thereof and tipiracil or a salt thereof using the same procedure for each substance.

Solution to Problem

The present inventors conducted extensive research and found a method that is capable of detecting a trifluridine- or tipiracil-related substance using the same procedure, rather than detecting these substances using different procedures, by subjecting a sample containing trifluridine or a salt thereof and tipiracil or a salt thereof to high-performance liquid chromatography using a mobile phase composed of an organic phase and an aqueous phase.

Therefore, the present invention typically provides the following Items 1 to 12.

1. A method for detecting a trifluridine-related substance or a tipiracil-related substance or both,
the method comprising the step of subjecting a sample containing trifluridine or a salt thereof and tipiracil or a salt thereof to high-performance liquid chromatography using a mobile phase composed of an organic phase and an aqueous phase.

2. The method according to Item 1, wherein the related substance is at least one member selected from the group consisting of the following related substances 1 to 5:
related substance 1: trifluorothymine,
related substance 2: 2-iminopyrrolidine,
related substance 3: 5-chloro-6-{(2-oxopyrrolidin-1-yl) methyl}pyrimidine-2,4-(1H,3H)-dione,
related substance 4: 2'-deoxy-5-methoxycarbonyluridine, and
related substance 5: 5-carboxyuracil.

3. The method according to Item 2, wherein the related substance comprises related substance 3, and the difference in retention time between related substance 3 and trifluridine in high-performance liquid chromatography is 1.0 minute or longer.

4. The method according to Item 2 or 3, wherein the percentage of the organic phase with respect to the entire mobile phase at retention times of related substances 1 to 5, trifluridine, and tipiracil is within a range of 7 to 15% by volume.

5. The method according to any one of Items 1 to 4, wherein the organic phase comprises methanol.

6. The method according to any one of Items 1 to 5, wherein the aqueous phase contains phosphoric acid or a salt thereof, or a mixture thereof.

7. The method according to any one of Items 2 to 6, wherein the difference between the maximum value and the minimum value of the percentage of the organic phase in the entire mobile phase at the retention times of related substances 1, 3, and 4 and trifluridine is 5% by volume or less with respect to the entire mobile phase.

8. The method according to any one of Items 1 to 7, wherein the mobile phase has a pH of 2.0 to 5.0.

9. The method according to any one of Items 1 to 8, wherein the mobile phase contains 1-heptanesulfonic acid or a salt thereof.

10. 2'-Deoxy-5-methoxycarbonyluridine (related substance 4) for use in quality control of a combination drug containing trifluridine or a salt thereof and tipiracil or a salt thereof.

11. 2'-Deoxy-5-methoxycarbonyluridine (related substance 4) for use as a standard in the detection of impurities in a combination drug containing trifluridine or a salt thereof and tipiracil or a salt thereof 12. A method for producing 2'-deoxy-5-methoxycarbonyluridine (related substance 4), the method comprising separating 2'-deoxy-5-methoxycarbonyluridine from a combination drug containing trifluridine or a salt thereof and tipiracil or a salt thereof.

Advantageous Effects of Invention

The present invention is capable of detecting a trifluridine-related substance and a tipiracil-related substance contained in a sample containing trifluridine or a salt thereof and tipiracil or a salt thereof by using the same procedure for each substance. Therefore, the method of the present invention makes it possible to simply and quickly perform quality control of a pharmaceutical preparation containing trifluridine or a salt thereof and tipiracil or a salt thereof.

DESCRIPTION OF EMBODIMENTS

Figure 1:
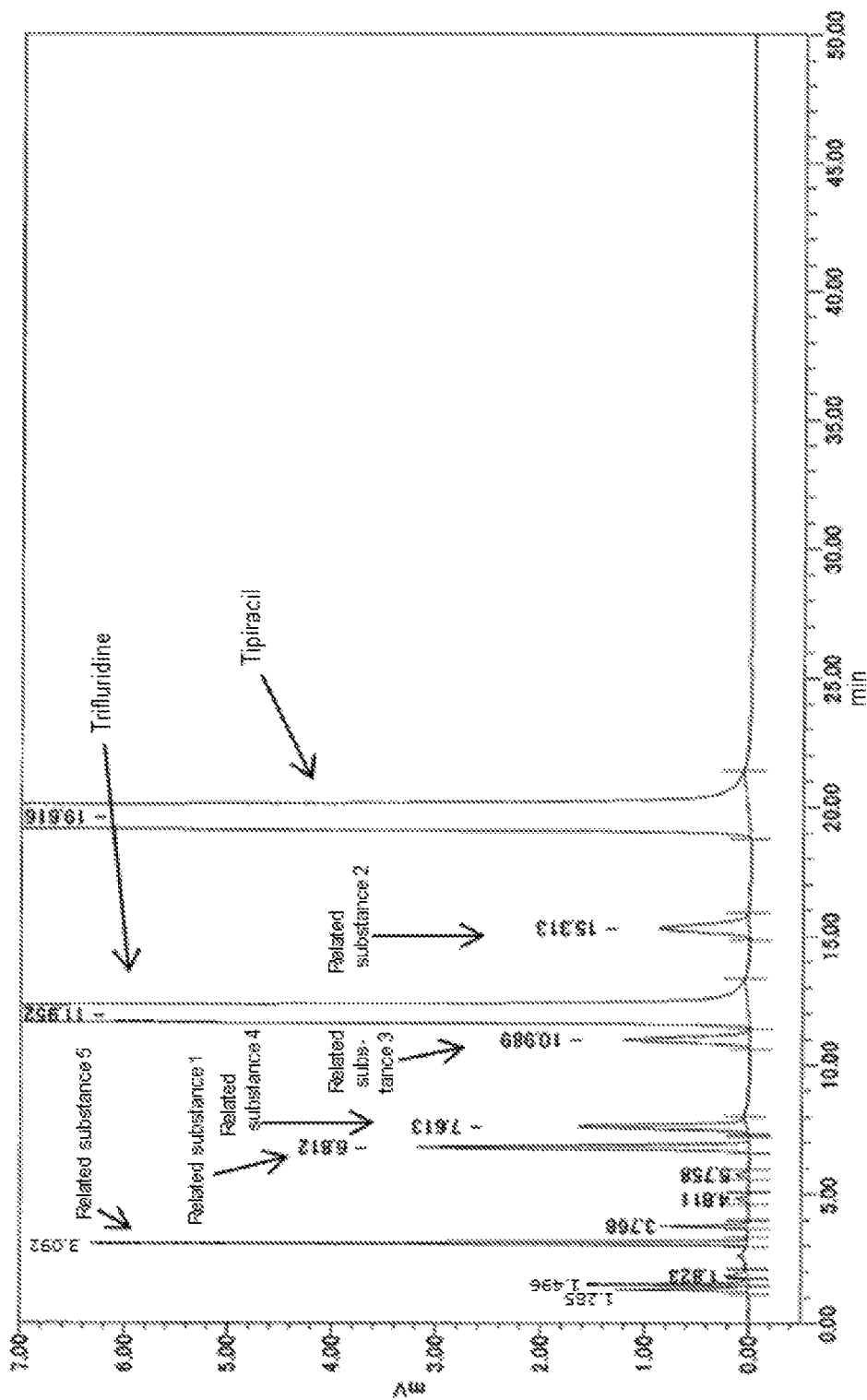
FIG. 1 shows the chromatogram obtained in Example 1.
Figure 2:
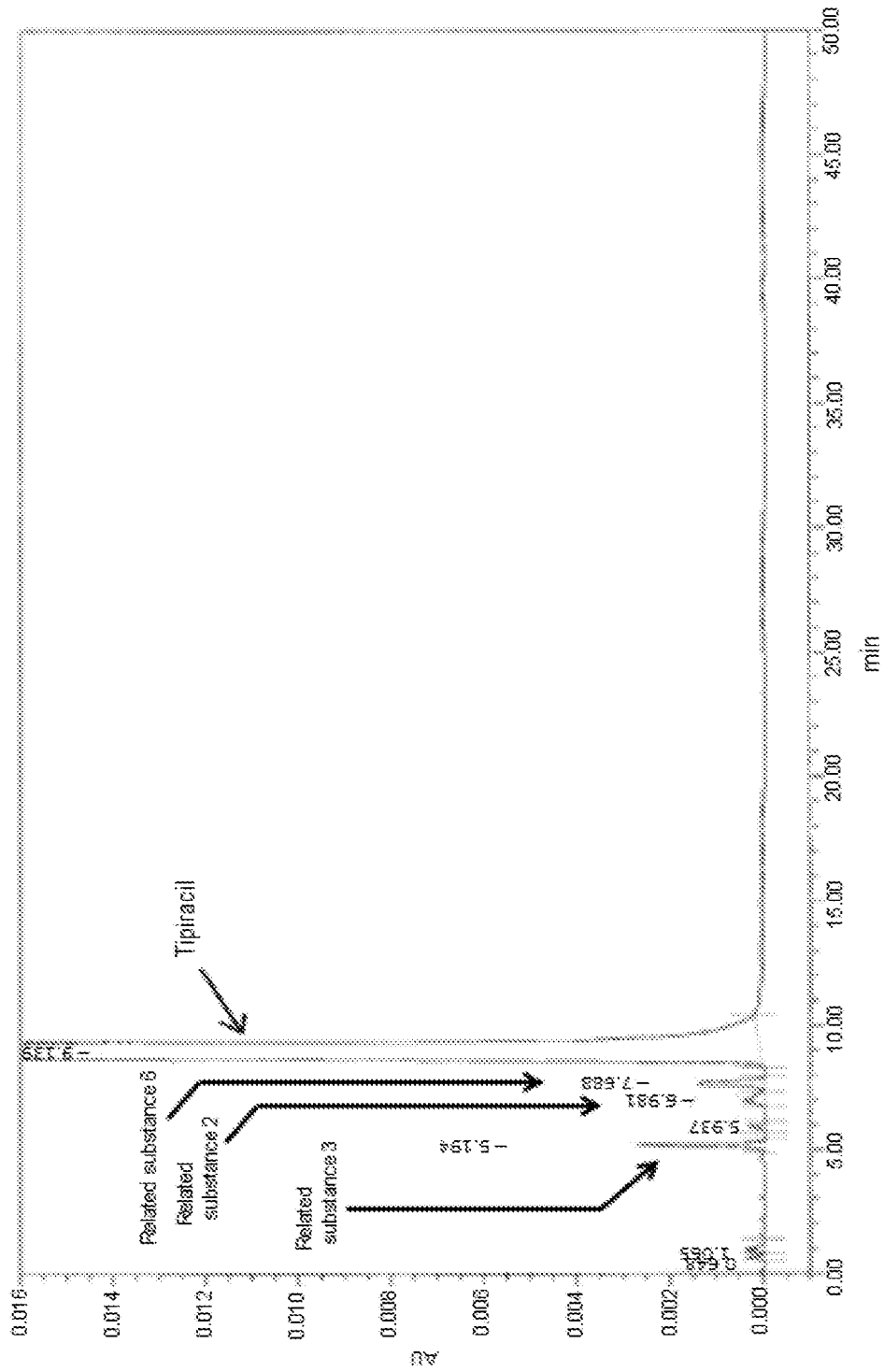
FIG. 2 shows the chromatogram obtained in Example 10.

Tipiracil (TPI) referred to in the present invention is 5-chloro-6-(2-iminopyrrolidin-1-yl)methyl-2,4(1H,3H)-pyrimidinedione and is a compound having the following structure:

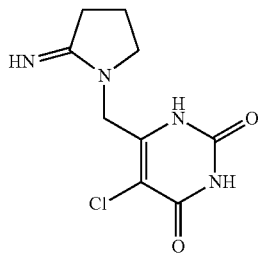 [SMILES: N=C1CCCN1Cc1[nH]c(=O)[nH]c(=O)c1Cl]

Trifluridine (FTD) referred to in the present invention is α,α,α,-trifluorothymidine and is a compound having the following structure:

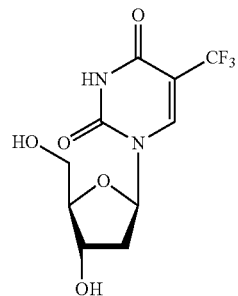 [SMILES: O=c1[nH]c(=O)n([C@H]2C[C@@H](O)[C@@H](CO)O2)cc1C(F)(F)F]

In the present invention, when trifluridine or tipiracil has isomers, such as optical isomers, stereoisomers, rotational isomers, and tautomers, any method that uses the isomers as a sample or uses a mixture of the isomers and tipiracil and/or trifluridine as a sample is also encompassed within the scope of the present invention, unless otherwise stated.

In the present invention, a salt refers to a pharmaceutically acceptable salt, unless otherwise stated, and may be a base addition salt or an acid addition salt.

Examples of base addition salts include alkali metal salts, such as sodium salts and potassium salts; alkaline earth metal salts, such as calcium salts and magnesium salts; ammonium salts; and organic amine salts, such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts, such as hydrochloride, sulfate, nitrate, phosphate, and perchlorate; organic acid salts, such as acetate, formate, maleate, fumarate, tartrate, citrate, ascorbate, and trifluoroacetate; and sulfonates, such as methanesulfonate, isethionate, benzenesulfonate, and p-toluenesulfonate.

The trifluridine or a salt thereof used in the present invention is preferably trifluridine in the free, non-salt form. The tipiracil or a salt thereof used in the present invention is preferably tipiracil hydrochloride. The sample containing trifluridine or a salt thereof and tipiracil or a salt thereof used in the present invention is preferably a sample containing trifluridine in the free form and tipiracil hydrochloride.

The method of the present invention is capable of detecting a trifluridine-related substance and a tipiracil-related substance by subjecting a sample containing trifluridine or a salt thereof and tipiracil or a salt thereof to high-performance liquid chromatography one time without the necessity of conducting a plurality of measurements. As long as the method is capable of detecting both trifluridine-related substances and tipiracil-related substances by a single measurement when the sample contains both of these substances, such a method is encompassed by the present invention even if the results confirm that neither of these related substances is detected because the sample contains either a trifluridine-related substance or a tipiracil-related substance or because the sample contains no such related substances.

The sample according to the present invention can contain trifluridine- or tipiracil-related substances. Examples of the related substances include the compounds shown as related substances 1 to 6.

| Related Substance | Compound Name | Structural Formula |
|---|---|---|
| 1 | Trifluorothymine | |
| 2 | 2-Iminopyrrolidine | |
| 3 | 5-Chloro-6-{(2-oxopyrrolidin-1-yl)methyl}pyrimidine-2,4-(1H,3H)-dione | |
| 4 | 2'-Deoxy-5-methoxycarbonyluridine | |
| 5 | 5-Carboxyuracil | |
| 6 | 5-Chloro-6-(chloromethyl)pyrimidine-2,4(1H,3H)-dione | |

Related substance 1 is trifluorothymine and is a trifluridine-related substance. Related substance 1 may be sometimes referred to as 5-(trifluoromethyl)pyrimidine-2,4(1H,3H)-dione.

Related substance 2 is 2-iminopyrrolidine and is a tipiracil-related substance.

Related substance 3 is 5-chloro-6-{(2-oxopyrrolidin-1-yl)methyl}pyrimidine-2,4-(1H,3H)-dione and is a tipiracil-related substance.

Related substance 4 is 2'-deoxy-5-methoxycarbonyluridine and is a trifluridine-related substance.

Related substance 4 may be sometimes referred to as 1-((2R,4R,5R)-4-hydroxy-5-(hydroxymethyl)tetrahydrofuran-2-yl)-2,4-dioxo-1,2,3,4-tetrahydropyrimidine-5-methyl carboxylate.

Related substance 5 is 5-carboxyuracil and is a trifluridine-related substance. Related substance 5 may be sometimes referred to as 2,4-dioxo-1,2,3,4-tetrahydropyrimidine-5-carboxylate.

Related substance 6 is 5-chloro-6-(chloromethyl)pyrimidine-2,4(1H,3H)-dione and is a tipiracil-related substance.

In addition to samples prepared from a pharmaceutical preparation or drug substance itself, it is possible in the present invention to use samples prepared in a test for determining stability etc., samples prepared by adding each related substance to study the retention time (peak of chromatogram) etc. of the substance, samples prepared to confirm the manufacturing process of a pharmaceutical preparation or drug substance, and the like.

The pharmaceutical preparation (sometimes referred to as "a combination drug," "composition," or the like) usable in the present invention contains trifluridine or a salt thereof and tipiracil or a salt thereof, optionally contains a pharmaceutically acceptable carrier, and may be formed into a suitable dosage form according to prevention and treatment purposes. Examples of the dosage form include oral preparations, injections, suppositories, ointments, patches, and the like, with oral preparations being preferable. Such dosage forms can be formed by methods conventionally known to persons skilled in the art.

As the pharmaceutically acceptable carrier, various conventional organic or inorganic carrier materials used as preparation materials may be incorporated as an excipient, binder, disintegrant, lubricant, or colorant in solid preparations; or as a solvent, solubilizing agent, suspending agent, isotonizing agent, buffer, or soothing agent in liquid preparations. It is also possible to use pharmaceutical preparation additives, such as antiseptics, antioxidants, colorants, sweeteners, and stabilizers, if required.

Oral solid preparations when prepared are produced by adding an excipient and optionally a binder, disintegrant, lubricant, colorant, taste-masking or flavoring agent, etc., to the compound of the present invention, and formulating the resulting mixture into tablets, coated tablets, granules, powders, capsules, or the like by ordinary methods.

The daily dose of the medicinal drug in such a dosage form may be suitably determined according to the condition, body weight, age, gender, etc., of the patient.

To perform high-performance liquid chromatography in the present invention, a commercially available chromatography device can be used.

In high-performance liquid chromatography, a medicinal drug can be analyzed by using a mixture of an organic phase and an aqueous phase as a mobile phase, and introducing it into a column. In the present invention, the sample contains trifluridine or a salt thereof and tipiracil or a salt thereof, thus requiring measurement conditions based on both trifluridine and tipiracil. If it were possible to measure trifluridine, trifluridine-related substances, tipiracil, and tipiracil-related substances under a single measurement condition for high-performance liquid chromatography, it would be very useful in terms of quality control.

Known columns for chromatography include normal-phase columns, in which an organic phase is used as the mobile phase to separate lipophilic compounds, and reversed-phase columns, in which an aqueous phase is used as the mobile phase to separate compounds. In high-performance liquid chromatography, a reversed-phase column is often used. In the present invention as well, reversed-phase chromatography is preferable.

The column for high-performance liquid chromatography usable in the present invention is selected from a silica gel column, a column containing silica gel whose surface is modified with octadecyl silyl groups (an ODS column or C18 column), a column containing silica gel whose surface is modified with octyl groups (a C8 column), a column containing silica gel whose surface is modified with cyanopropyl groups (a CN column), a column containing silica gel whose surface is modified with phenethyl groups (a Ph column), a column containing silica gel whose surface is modified with aminopropyl groups (an NH column), a column containing silica gel whose surface is modified with dihydroxypropyl groups (a Diol column), a column packed with various polymers (a polymer column), a column packed with ion-exchange resin (an ion-exchange column), and the like. In the present invention, an ODS column is preferable.

It is possible to use various types of ODS columns with different silica gel particle sizes, different pore sizes, different types of bonding of octadecyl silyl groups, different degrees of substitution of octadecyl silyl groups, etc. In the present invention, the silica gel preferably has an average particle size of, for example, 2 to 10 µm, and more preferably 3 to 5 µm. The average particle size of silica gel can be measured by, for example, laser diffractometry. The silica gel has an average pore size of, for example, 6 to 20 nm, and more preferably 8 to 13 nm. The average pore size of silica gel can be measured by a gas absorption method etc. The bonding type of octadecyl silyl groups in the silica gel is preferably, for example, monomeric or polymeric. The carbon content in the silica gel is preferably, for example, 3 to 25%, more preferably 8 to 25%, and more preferably 10 to 20%. The carbon content in the silica gel can be measured by various methods. In the present invention, to improve the shape of the peaks of and to more easily separate tipiracil, which is a basic compound, and tipiracil-related substances from each other, it is preferable to use an ODS column (an end-capped ODS column) in which residual silanol obtained after octadecylation is treated with a low-molecular-weight silylating agent, it is more preferable to use an ODS column that is end-capped to achieve the carbon content of 10% or more, and it is particularly preferable to use a Wakosil-II 5C18 RS (produced by Wako Pure Chemical Industries, Ltd.) or an Inertsil ODS-4 (produced by GL Sciences Inc.).

Examples of the organic phase in the mobile phase in high-performance liquid chromatography include non-polar solvents, such as hexane, cyclohexane, heptane, diethyl ether, tetrahydrofuran, chloroform, and methylene chloride; aprotic polar solvents, such as acetone, dimethylsulfoxide, and acetonitrile; acetic acid; methanol; ethanol; isopropanol; acetonitrile; and the like. These solvents may be used alone, or two or more of these solvents may be used as a mixed solvent. The organic phase according to the present invention is preferably methanol or acetonitrile, and more preferably methanol. The organic phase may contain 10% or less of water.

The aqueous phase used in the mobile phase in high-performance liquid chromatography may contain 10% or less of the organic solvent mentioned above in addition to water, but preferably contains only water.

To enable reproducibility, various buffers can be added to the mobile phase in high-performance liquid chromatography. For example, it is possible to add acetic acid or a salt thereof, citric acid or a salt thereof, tartaric acid or a salt thereof, and phosphoric acid or a salt thereof. Examples of acetic acid or a salt thereof include acetic acid and sodium acetate. Examples of citric acid or a salt thereof include citric acid, monosodium citrate, disodium citrate, and trisodium citrate. Examples of tartaric acid or a salt thereof include tartaric acid and sodium tartrate. Examples of phosphoric acid or a salt thereof include phosphoric acid, sodium dihydrogenphosphate, disodium hydrogenphosphate, potassium dihydrogen phosphate, and dipotassium hydrogen phosphate. Additives in the aqueous phase according to the present invention are preferably phosphoric acid or a salt thereof, and more preferably phosphoric acid and sodium dihydrogenphosphate, from the viewpoint of the properties of the substances to be measured, the shape of the peaks obtained by the measurement, as well as the measurement reproducibility. These additives may be used alone or in a combination of two or more.

The concentration of the buffer that can be used in the present invention may be suitably adjusted within a concentration range in which the buffer does not undergo precipitation during the high-performance liquid chromatography measurement. The concentration is preferably 1 to 50 mM, more preferably 5 to 20 mM, and particularly preferably 9 to 11 mM.

For high-performance liquid chromatography, a mixture of an organic phase and an aqueous phase is used as the mobile phase. In the present invention, the percentage of the organic phase in the entire mobile phase is preferably within a range of 5 to 20% by volume, and more preferably 7 to 15% by volume, with respect to the entire mobile phase at the retention time of at least one substance selected from the group consisting of related substances 1, 3, and 4 and trifluridine (preferably the retention times of related substances 1, 3, and 4 and trifluridine). Moreover, in the present invention, the percentage of the organic phase in the entire mobile phase is particularly preferably within a range of 7 to 15% by volume with respect to the entire mobile phase at the retention times of related substances 1, 2, 3, and 4, trifluridine, and tipiracil.

In the present invention, it is more preferable that the mobile phase is composed of methanol and an aqueous phase, and that the percentage of methanol in the entire mobile phase is within a range of 5 to 20% by volume with respect to the entire mobile phase at the retention time of at least one substance selected from the group consisting of related substances 1, 3, and 4 and trifluridine (preferably at the retention times of related substances 1, 3, and 4 and trifluridine). It is more preferable that the mobile phase is composed of methanol and an aqueous phase containing phosphoric acid or sodium dihydrogenphosphate, and that the percentage of methanol in the entire mobile phase is within a range of 5 to 20% by volume with respect to the entire mobile phase at the retention time of at least one substance selected from the group consisting of related substances 1, 3, and 4 and trifluridine (preferably at the retention times of related substances 1, 3, and 4 and trifluridine). It is particularly preferable that the mobile phase is composed of methanol and an aqueous phase containing phosphoric acid or sodium dihydrogenphosphate, and that the percentage of methanol in the entire mobile phase is within a range of 7 to 15% by volume with respect to the entire mobile phase at the retention time of at least one substance selected from the group consisting of related substances 1, 3, and 4 and trifluridine (preferably at the retention times of related substances 1, 3, and 4 and trifluridine).

As the mobile phase in high-performance liquid chromatography, a mixture of an organic phase and an aqueous phase is used. The ratio thereof is often made to vary during the measurement, and this is referred to as a gradient application. The gradient application is usually performed often in consideration of the retention time of the target compound and the separation of the target compound and related substances from each other.

In the present invention, the difference between the maximum value and the minimum value of the percentage of the organic phase in the entire mobile phase at the retention times of the related substances 1, 3, and 4 and trifluridine is preferably 5% by volume or less, and particularly preferably 1% by volume or less, with respect to the entire mobile phase, and isocratic state is more particularly preferable. Further, in the present invention, the change in the percentage of the organic phase in the entire mobile phase during the measurement (the difference between the maximum value and the minimum value of the percentage of the organic phase in the entire mobile phase during the measurement) is preferably 5% by volume or less, and particularly preferably 1% by volume or less with respect to the entire mobile phase, and isocratic state is more particularly preferable.

In the present invention, in addition to the additives above, it is possible to add an ion-pair reagent, which plays a key role in retaining related substances in the column. Examples of ion-pair reagents include sodium alkylsulfonates (preferably linear or branched sodium alkylsulfonates having 7 to 12 carbon atoms), such as sodium propylsulfonate, sodium butylsulfonate, sodium pentanesulfonate, sodium hexanesulfonate, sodium heptanesulfonate, sodium octanesulfonate, and sodium dodecanesulfonate; sodium dodecyl sulfate; quaternary ammonium salts, such as tetraethyl ammonium hydroxide, tetrabutyl ammonium hydroxide, tetrabutyl ammonium chloride, and tetrabutyl ammonium bromide; and tertiary amines, such as trihexylamine and trioctylamine. The ion-pair reagent according to the present invention is preferably a linear or branched sodium alkylsulfonate having 7 to 12 carbon atoms, and more preferably sodium heptanesulfonate. These ion-pair reagents may be used alone or in a combination of two or more.

The pH of the mobile phase according to the present invention can be suitably adjusted with the addition of the additives mentioned above, and is preferably 2.0 to 5.0, and more preferably 2.6 to 2.8.

The detection wavelength usable in the present invention may be 205 to 230 nm, preferably 208 to 220 nm, and more preferably 208 to 212 nm, in consideration of the properties of each related substance.

The temperature of the mobile phase in the column used in the method of the present invention may be suitably set. In consideration of the effect from the external environment, reproducibility, and the like, the temperature is preferably maintained constant, and is more preferably 25 to 50° C., still more preferably 35 to 45° C., and particularly preferably 38 to 42° C. To maintain the temperature constant, the temperature of the entire column is controlled, and in addition, a preheated mixer or the like can be used.

In the high-performance liquid chromatography according to the present invention, the flow rate, injection amount, etc., of the mobile phase may be suitably changed. In the present invention, the flow rate of the mobile phase is preferably, but not particularly limited to, 0.5 to 2.0 mL/min, and more preferably 0.7 to 1.3 mL/min.

The related substances of the present invention may be synthesized by known methods or may be obtained from commercially available products. Related substances can be identified by comparing the retention times in high-performance liquid chromatography, mass spectra, and spectra from a photodiode array (PDA) between the thus-obtained related substances and the related substances detected in accordance with the present invention.

Further, these related substances can be quantitatively measured by either an external standard method or internal standard method.

When these related substances are possibly contained as impurities in a medicinal drug or pharmaceutical preparation, these related substances are regulated in accordance with guideline ICH-Q3A of the International Council for Harmonisation of Technical Requirements for Pharmaceuticals for Human Use. The method of the present invention is very useful since it is possible to confirm whether the standard of the guideline is satisfied.

Further, these related substances can be detected from trifluridine or a salt thereof and tipiracil or a salt thereof using the method of the present invention. Further, in the present invention, at least one substance selected from related substances 1 to 5, and preferably related substance 4, can be used as a standard of quality control.

Trifluridine, tipiracil, and related substances thereof used as a standard are of high purity; the purity when used as a standard is preferably 99.0% or higher, and more preferably 99.9% or higher. Therefore, the related substances separated under the conditions described above for high-performance liquid chromatography can be used as a standard. That is, the present invention may also be referred to as a method for producing the related substances, the method comprising separating the related substances from a combination drug containing trifluridine or a salt thereof and tipiracil or a salt thereof. These related substances may be related substances 1 to 5 mentioned above, with related substance 4 being preferable.

In the present invention, a method of high-performance liquid chromatography is used to detect trifluridine- or tipiracil-related substances.

The method preferably uses high-performance liquid chromatography in which the organic phase content is 5 to 20% by volume in the entire mobile phase at the retention times of the related substances 1, 3, and 4 and trifluridine.

The method more preferably uses high-performance liquid chromatography in which the mobile phase is composed of methanol and an aqueous phase, and the methanol content is 5 to 20% by volume in the entire mobile phase at the retention times of related substances 1, 3, and 4 and trifluridine.

The method more preferably uses high-performance liquid chromatography in which the mobile phase is composed of methanol and an aqueous phase containing phosphoric acid or sodium dihydrogenphosphate, and the methanol content is 5 to 20% in the entire mobile phase at the retention times of related substances 1, 3, and 4 and trifluridine.

The method more preferably uses high-performance liquid chromatography in which the mobile phase is composed of methanol and an aqueous phase containing phosphoric acid or sodium dihydrogenphosphate, and the methanol content is 7 to 15% in the entire mobile phase at the retention times of related substances 1, 3, and 4 and trifluridine.

The method more preferably uses high-performance liquid chromatography in which the mobile phase is composed of methanol and an aqueous phase containing phosphoric acid or sodium dihydrogenphosphate, the methanol content is 7 to 15% in the entire mobile phase at the retention times of related substances 1, 3, and 4 and trifluridine, and the change in the ratio of the organic phase to the aqueous phase is 5% or less with respect to the entire mobile phase during the measurement.

The method more preferably uses high-performance liquid chromatography in which the mobile phase is composed of methanol and an aqueous phase containing phosphoric acid or sodium dihydrogenphosphate, the methanol content is 7 to 15% in the entire mobile phase at the retention times of related substances 1, 3, and 4 and trifluridine, the change in the ratio of the organic phase to the aqueous phase is 5% or less with respect to the entire mobile phase during the measurement, and 1-sodium heptanesulfonate is used as an ion-pair reagent.

In the present invention, if trifluridine and tipiracil have an overly short retention time, it is impossible to separate related substances 1 to 5. Further, if trifluridine and tipiracil have an overly long retention time, the measurement takes a long time. In the present invention, the retention time of trifluridine is, for example, 5 to 30 minutes, and preferably 5 to 20 minutes. Further, in the present invention, the retention time of tipiracil is, for example, 5 to 30 minutes, and preferably 10 to 25 minutes.

In the present invention, the retention times of related substance 1 and related substance 4 tend to be very close to each other in high-performance liquid chromatography. To avoid such a situation, the difference in the retention time between related substance 1 and related substance 4 is, for example, 0.2 minutes or longer, preferably 0.4 minutes or longer, and more preferably 0.5 minutes or longer.

The retention times of related substance 3 and trifluridine also tend to be very close to each other in high-performance liquid chromatography. To avoid such a situation, the difference in the retention time between related substance 3 and trifluridine is, for example, 0.2 minutes or longer, preferably 0.5 minutes or longer, and more preferably 1.0 minute or longer.

Further, the present invention, which enables the detection of trifluridine- or tipiracil-related substances, also enables individual detection of only trifluridine-related substances from trifluridine or a salt thereof, as well as individual detection of only tipiracil-related substances from tipiracil or a salt thereof.

The method for detecting only trifluridine-related substances from trifluridine or a salt thereof is in accordance with the above method for detecting a trifluridine-related substance or a tipiracil-related substance or both from trifluridine or a salt thereof and tipiracil or a salt thereof; preferable embodiments of the method for detecting only trifluridine-related substances from trifluridine or a salt thereof are the same as this method.

The method for detecting only tipiracil-related substances from tipiracil or a salt thereof is in accordance with the above method for detecting a trifluridine-related substance or a tipiracil-related substance or both from trifluridine or a salt thereof and tipiracil or a salt thereof. Therefore, in addition to the embodiments described below, the embodiments described above can be applied.

When the present invention is used as a method for detecting only tipiracil-related substances from tipiracil or a salt thereof, the same column as that used above is used in high-performance liquid chromatography, with an ODS column being preferable, and Wakosil-II 5C18 RS (produced by Wako Pure Chemical Industries, Ltd.) or Inertsil ODS-3 (produced by GL Sciences Inc.) being more preferable.

The organic phase in the mobile phase in high-performance liquid chromatography may be the organic solvent mentioned above, preferably methanol or acetonitrile, and more preferably acetonitrile.

The aqueous phase in the mobile phase in high-performance liquid chromatography may contain 10% or less of the organic solvent, in addition to water, but preferably contains only water.

To enable reproducibility, various buffers may be added to the mobile phase in high-performance liquid chromatography. Examples of usable buffers include the additives mentioned above, with phosphoric acid or a salt thereof being preferable, and potassium dihydrogen phosphate being more preferable.

The buffer may be used at a concentration mentioned above, preferably 1 to 50 mM, more preferably 2 to 20 mM, and particularly preferably 3 to 10 mM.

In high-performance liquid chromatography, the mixture of the organic phase above and the aqueous phase above is used as the mobile phase, and the percentage of the organic phase is preferably within a range of 5 to 20% by volume, and more preferably 7 to 15% by volume, with respect to the entire mobile phase at the retention time of related substance 3 or tipiracil (preferably at the retention times of related substance 3 and tipiracil).

In high-performance liquid chromatography, the mobile phase is preferably composed of acetonitrile and an aqueous phase, the percentage of the acetonitrile in the entire mobile phase is within a range of 5 to 20% by volume with respect to the entire mobile phase at the retention time of related substance 3 or tipiracil (preferably at the retention times of related substance 3 and tipiracil). The mobile phase is more preferably composed of acetonitrile and an aqueous phase containing phosphoric acid or a salt thereof, and the percentage of the acetonitrile in the entire mobile phase is within a range of 5 to 20% by volume with respect to the entire mobile phase at the retention times of related substance 3 and tipiracil. The mobile phase is more particularly preferably composed of acetonitrile and an aqueous phase containing phosphoric acid or sodium dihydrogenphosphate, and the percentage of acetonitrile in the entire mobile phase is within a range of 7 to 15% by volume with respect to the entire mobile phase at the retention times of related substance 3 and tipiracil.

An ion-pair reagent may be added to the mobile phase in high-performance liquid chromatography. Examples of the ion-pair reagent include those mentioned above. The ion-pair reagent is preferably sodium alkylsulfonate, more preferably sodium alkylsulfonate having 4 to 12 carbon atoms, and particularly preferably sodium heptanesulfonate.

The flow rate of the mobile phase in high-performance liquid chromatography is not particularly limited, and preferably 0.5 to 2.0 mL/min, more preferably 0.6 to 1.5 mL/min, and particularly preferably 0.7 to 1.3 mL/min.

In the measurement of tipiracil-related substances by high-performance liquid chromatography, it is sufficient if related substances 2, 3, and 6 and tipiracil are separated from each other. The retention time of each related substance varies depending on the conditions. It is sufficient as long as the difference in the retention time between each substance is 0.5 minutes or longer.

A method of high-performance liquid chromatography is used to detect tipiracil-related substances from tipiracil or a salt thereof.

The method preferably uses high-performance liquid chromatography in which the organic phase content is 5 to 20% by volume in the entire mobile phase at the retention times of related substance 3 and tipiracil.

The method more preferably uses high-performance liquid chromatography in which the organic phase comprises acetonitrile, and the acetonitrile content is 5 to 20% by volume in the entire mobile phase at the retention times of related substance 3 and tipiracil.

The method more preferably uses high-performance liquid chromatography in which the mobile phase is composed of acetonitrile and an aqueous phase containing phosphoric acid or potassium dihydrogen phosphate, and the acetonitrile content is 5 to 20% in the entire mobile phase at the retention times of related substance 3 and tipiracil.

The method more preferably uses high-performance liquid chromatography in which the mobile phase is composed of acetonitrile and an aqueous phase containing phosphoric acid or potassium dihydrogen phosphate, and the acetonitrile content is 7 to 15% in the entire mobile phase at the retention times of related substance 3 and tipiracil.

The method more preferably uses high-performance liquid chromatography in which the mobile phase is composed of acetonitrile and an aqueous phase containing potassium dihydrogen phosphate, the acetonitrile content is 7 to 15% in the entire mobile phase at the retention times of related substance 3 and tipiracil, and the change in the ratio of the organic phase to the aqueous phase is 5% or less with respect to the entire mobile phase during the measurement.

The method more preferably uses high-performance liquid chromatography in which the mobile phase is composed of acetonitrile and an aqueous phase containing potassium dihydrogen phosphate, the acetonitrile content is 7 to 15% in the entire mobile phase at the retention times of related substance 3 and tipiracil, the change in the ratio of the organic phase to the aqueous phase is 5% or less with respect to the entire mobile phase during the measurement, and 1-sodium heptanesulfonate is used as an ion-pair reagent.

As described above, the method of the present invention enables the separation of trifluridine-related substances from trifluridine or a salt thereof and enables the detection of the trifluridine-related substances. Further, the method of the present invention enables the separation of tipiracil-related substances from tipiracil or a salt thereof, and enables the detection of the tipiracil-related substances. Furthermore, the method of the present invention enables the separation of trifluridine- and tipiracil-related substances, each of these substances individually, and enables the detection of these substances. Therefore, by the use the present invention in the production control of compositions containing trifluridine or a salt thereof and tipiracil or a salt thereof, it is possible to obtain a composition containing reduced amounts of the related substances. As described above, the retention times of related substance 1 and related substance 4 tend to be very close to each other in high-performance liquid chromatography. Further, the retention times of related substance 3 and trifluridine also tend to be very close to each other in high-performance liquid chromatography. Therefore, an invention relating to the separation of these related substances is particularly useful.

For example, by the use of the present invention, it is possible to obtain a combination drug that contains trifluridine or a salt thereof and tipiracil or a salt thereof, but does not substantially contain the related substances mentioned above (e.g., related substance 4). Further, by the use of the present invention, it is possible to obtain a combination drug containing trifluridine or a salt thereof and tipiracil or a salt thereof, and containing the related substances (e.g., related substance 4) wherein the amount (mass) of the related substances (e.g., related substance 4) is 0.05 mass % or less with respect to the entire trifluridine contained in the combination drug. In such embodiments, the lower limit of the content (mass) of the related substance (e.g., related substance 4) in the combination drug is not particularly limited. Therefore, in the present invention, the related substances above (e.g., related substance 4) may be used for the quality control of the combination drug containing trifluridine or a salt thereof and tipiracil or a salt thereof (e.g., for the management (adjustment) of the amount of the related substances). Further, by the use of the present invention, the related substances above (e.g., related substance 4) may be used as a standard for detecting impurities in a combination drug containing trifluridine or a salt thereof and tipiracil or a salt thereof. Moreover, the present invention can provide a method for producing the related substances above (e.g., related substance 4), the method comprising separating these related substances from a combination drug containing trifluridine or a salt thereof and tipiracil or a salt thereof. These effects of the present invention apply not only to related substance 4 but also to related substances 1 to 3, 5, and 6.

EXAMPLES

Measurement was performed by high-performance liquid chromatography under the following test conditions.

Detector: Ultraviolet spectrophotometer (wavelength: 210 nm)
Column: An octadecylsilyl silica gel column for liquid chromatography (5 μm) was placed in a stainless steel column with an inner diameter of 4.6 mm and a length of 15 cm.
Column temperature: 40° C.
Flow rate: 0.6 to 1.0 mL/min.
Mobile phase: stated in each Example.
Gradient: stated in each Example.

The samples to be measured by high-performance liquid chromatography were prepared as follows.

Trifluridine and tipiracil hydrochloride were dissolved in a solution having the same composition as that of a mobile phase to be used under each of the measurement conditions, and the resulting product was suitably diluted so that the trifluridine concentration was about 1 mg/mL and the tipiracil hydrochloride concentration was about 0.5 mg/mL, thus obtaining samples.

Example 1

Column: Inertsil ODS-4, produced by GL Sciences Inc.
Mobile phase: Sodium dihydrogenphosphate dihydrate (1.4 g) and 1-sodium heptanesulfonate (0.9 g) were dissolved in water (900 mL), and phosphoric acid was added thereto to adjust the pH to 2.7. Methanol (100 mL) was added to this solution to obtain a mobile phase.

FIG. 1 shows the measurement results. The retention time of trifluridine was thus confirmed to be 12.0 minutes, and the retention time of tipiracil was confirmed to be 19.6 minutes. Moreover, the retention time of related substance 1 was confirmed to be 6.8 minutes, the retention time of related substance 4 was confirmed to be 7.6 minutes, the retention time of related substance 3 was confirmed to be 11.0 minutes, and the retention time of related substance 2 was confirmed to be 15.3 minutes. Additionally, the retention time of related substance 5 was confirmed to be 3.1 minutes. The results confirmed that the measurement conditions above achieved the separation of related substance 1 from related substance 4, as well as the separation of related substance 3 from trifluridine.

The retention time of each of the related substances detected here was consistent with the retention time of each related substance separately purchased or synthesized, which confirmed that the related substances detected here were compounds having the structures of related substances 1 to 6.

Example 2

Column: Inertsil ODS-4, produced by GL Sciences Inc.
Mobile phase: Sodium dihydrogenphosphate dihydrate (1.5 g) and 1-sodium heptanesulfonate (0.9 g) were dissolved in water (900 mL), and phosphoric acid was added thereto to adjust the pH to 2.7. Methanol (100 mL) was added to this solution to obtain a mobile phase.
The same measurement results were obtained as in Example 1.

Example 3

Column: Inertsil ODS-4, produced by GL Sciences Inc.
Mobile phase: Sodium dihydrogenphosphate dihydrate (1.4 g) and 1-sodium heptanesulfonate (1.0 g) were dissolved in water (900 mL), and phosphoric acid was added thereto to adjust the pH to 2.8. Methanol (100 mL) was added to this solution to obtain a mobile phase.
The same measurement results were obtained as in Example 1.

Example 4

Column: Inertsil ODS-4, produced by GL Sciences Inc.
Mobile phase: Sodium dihydrogenphosphate dihydrate (1.4 g) and 1-sodium heptanesulfonate (0.9 g) were dissolved in water (900 mL), and phosphoric acid was added thereto to adjust the pH to 2.7. Methanol (95 mL) was added to this solution to obtain a mobile phase.
The same measurement results were obtained as in Example 1.

Example 5

Column: Wakosil-II 5C18 RS, produced by Wako Pure Chemical Industries, Ltd.
Mobile phase: Sodium dihydrogenphosphate dihydrate (1.4 g) and 1-sodium heptanesulfonate (0.9 g) were dissolved in water (900 mL), and phosphoric acid was added thereto to adjust the pH to 2.7. Methanol (100 mL) was added to this solution to obtain a mobile phase.
The same measurement results were obtained as in Example 1.

Example 6

Column: Wakosil-II 5C18 RS, produced by Wako Pure Chemical Industries, Ltd.
Mobile phase: Sodium dihydrogenphosphate dihydrate (3.1 g) and 1-sodium heptanesulfonate (2.0 g) were dissolved in water (2000 mL), and phosphoric acid was added thereto to adjust the pH to 2.7. Methanol (50 mL) was added to this solution (950 mL) to obtain a mobile phase.
The measurement results confirmed that the retention time of trifluridine was within a range of 21.0 to 23.0 minutes, and the retention time of tipiracil was within a range of 41.0 to 43.0 minutes. Additionally, the retention time of related substance 1 was confirmed to be within a range of 9.0 to 10.0 minutes, the retention time of related substance 4 was confirmed to be within a range of 8.0 to 9.0 minutes, the retention time of related substance 3 was confirmed to be within a range of 15.0 to 17.0 minutes, and the retention time of related substance 2 was confirmed to be within a range of 28.0 to 30.0 minutes.

Example 7

Column: Wakosil-II 5C18 RS, produced by Wako Pure Chemical Industries, Ltd.
Mobile phase: Potassium dihydrogen phosphate (1.25 g) and 1-sodium heptanesulfonate (1.01 g) were dissolved in water (920 mL), and acetonitrile (80 mL) was added thereto to obtain a mobile phase.
The measurement results confirmed that the retention time of trifluridine was 8.4 minutes, and the retention time of tipiracil was 12.2 minutes. Further, the retention time of related substance 1 was confirmed to be 6.1 minutes.

Example 8

Column: Inertsil ODS-3, produced by GL Sciences Inc.
Mobile phase: 1-Sodium heptanesulfonate (1.88 g) was dissolved in water (1860 mL), and acetonitrile (140 mL)

was added thereto, followed by the addition of phosphoric acid to adjust the pH to 2.7.

The measurement results confirmed that the retention time of trifluridine was 13.1 minutes, and the retention time of tipiracil was 24.7 minutes. Further, the retention time of related substance 1 was confirmed to be 8.6 minutes, the retention time of related substance 3 was confirmed to be 10.3 minutes, and the retention time of related substance 2 was confirmed to be 17.1 minutes.

Example 9

Column: Wakosil-II 5C18 RS, produced by Wako Pure Chemical Industries, Ltd.
Mobile phase: 1-Sodium heptanesulfonate (1.01 g) was weighed, and water was added thereto so that the total was 1000 mL. Methanol (150 mL) was added to this solution (850 mL), followed by the addition of phosphoric acid to adjust the pH to 2.7.

The measurement results confirmed that the retention time of trifluridine was within a range of 8.0 to 10.0 minutes, and the retention time of tipiracil was within a range of 14 to 17 minutes. Further, the retention time of related substance 3 was confirmed to be 6.3 minutes.

Example 10

Tipiracil hydrochloride was dissolved in a water-acetonitrile mixed solution (23:2) and suitably diluted so that the concentration of tipiracil hydrochloride was about 0.8 mg/mL, to thus obtain a sample containing tipiracil alone.
Column: Wakosil-II 5C18 RS, produced by Wako Pure Chemical Industries, Ltd., or Inertsil ODS-3, produced by GL Sciences Inc.
Mobile phase: Potassium dihydrogen phosphate (1.25 g) and 1-sodium heptanesulfonate (1.01 g) were dissolved in water (920 mL), followed by the addition of acetonitrile (80 mL) to obtain a mobile phase.

The measurement results confirmed that the retention time of tipiracil was 9.1 minutes. Further, the retention time of related substance 3 was confirmed to be 5.2 minutes, the retention time of related substance 2 was confirmed to be 7.0 minutes, and the retention time of related substance 6 was confirmed to be 7.7 minutes. The results confirmed that the measurement conditions achieved the separation of related substances 2, 3, and 6, and tipiracil from each other.

The invention claimed is:

1. A method for detecting a trifluridine-related substance or a tipiracil-related substance or both,
    subjecting a sample containing trifluridine or a salt thereof and tipiracil or a salt thereof to high-performance liquid chromatography with a mobile phase comprising an organic phase and an aqueous phase; and
    detecting at least one trifluridine-related or tipiracil-related substance contained in the sample,
    wherein the at least one trifluridine-related or tipiracil-related substance includes 2' deoxy-5-methoxycarbonyluridine being a related substance 4.

2. The method according to claim 1, wherein
the detecting comprises detecting related substances 2 and 5 as well as the related substances 1, 3 and 4 contained in the sample, the related substance 1 is trifluorothymine, the related substance 2 is 2-iminopyrrolidine, the related substance 3 is 5-chloro-6-{(2-oxopyrrolidin-1-yl)methyl}pyrimidine-2,4-(1H,3H)-dione, and the related substance 5 is 5-carboxyuracil.

3. The method according to claim 2, wherein the subjecting comprises performing the high-performance liquid chromatography such that the difference in retention time between the related substance 3 and trifluridine is 1.0 minute or longer.

4. The method according to claim 2, wherein the percentage of the organic phase with respect to the entire mobile phase at retention times of the related substances 1 to 5, trifluridine, and tipiracil is within a range of 7 to 15% by volume.

5. The method according to claim 2, wherein the organic phase comprises methanol.

6. The method according to claim 2, wherein the aqueous phase comprises phosphoric acid or a salt thereof, or a mixture thereof.

7. The method according to claim 2, wherein the difference between the maximum value and the minimum value of the percentage of the organic phase in the entire mobile phase at the retention times of the related substances 1, 3, and 4 and trifluridine is 5% by volume or less with respect to the entire mobile phase.

8. The method according to claim 2, wherein the mobile phase has a pH of 2.0 to 5.0.

9. The method according to claim 3, wherein the percentage of the organic phase with respect to the entire mobile phase at retention times of the related substances 1 to 5, trifluridine, and tipiracil is within a range of 7 to 15% by volume.

10. The method according to claim 3, wherein the organic phase comprises methanol.

11. The method according to claim 4, wherein the organic phase comprises methanol.

12. The method according to claim 3, wherein the aqueous phase comprises phosphoric acid or a salt thereof, or a mixture thereof.

13. The method according to claim 4, wherein the aqueous phase comprises phosphoric acid or a salt thereof, or a mixture thereof.

14. The method according to claim 3, wherein the difference between the maximum value and the minimum value of the percentage of the organic phase in the entire mobile phase at the retention times of the related substances 1, 3, and 4 and trifluridine is 5% by volume or less with respect to the entire mobile phase.

15. The method according to claim 4, wherein the difference between the maximum value and the minimum value of the percentage of the organic phase in the entire mobile phase at the retention times of the related substances 1, 3, and 4 and trifluridine is 5% by volume or less with respect to the entire mobile phase.

16. The method according to claim 3, wherein the mobile phase has a pH of 2.0 to 5.0.

17. The method according to claim 4, wherein the mobile phase has a pH of 2.0 to 5.0.

18. The method according to claim 1, wherein the mobile phase has a pH of 2.6 to 2.8.

19. The method according to claim 1, wherein the detecting comprises detecting at least one trifluridine-related substance and at least one tipiracil-related substance, and trifluorothymine is detected as a trifluridine-related substance, 5-chloro-6-{(2-oxopyrrolidin-1-yl)methyl}pyrimidine-2,4-(1H,3H)-dione is detected as a tipiracil-related substance, and 2'-deoxy-5-methoxycarbonyluridine is detected a trifluridine-related substance.

20. The method according to claim 1, wherein the detecting further comprises detecting at least one selected from the group consisting of trifluorothymine being a related substance 1, and 5-chloro-6-{(2-oxopyrrolidin-1-yl)methyl}pyrimidine-2,4-(1H,3H)-dione being a related substance 3.

21. The method according to claim 1, wherein the detecting further comprises detecting at least one selected from the group consisting of trifluorothymine being a related substance 1, 2-iminopyrrolidine being a related substance 2, 5-chloro-6-{(2-oxopyrrolidin-1-yl)methyl}pyrimidine-2,4-(1H,3H)-dione being a related substance 3, and 5-carboxyuracil being a related substance 5.

* * * * *